United States Patent
Butler et al.

(10) Patent No.: US 7,984,643 B2
(45) Date of Patent: Jul. 26, 2011

(54) PROCESS FOR EVALUATING FOULING CAUSED BY REFINERY FEEDSTOCKS

(75) Inventors: Graham Butler, Surrey (GB); John William Couves, Buckinghamshire (GB); Paul Greenough, Buckinghamshire (GB); Nicholas John Gudde, Surrey (GB); Michael Graham Hodges, Surrey (GB)

(73) Assignee: BP Oil International Limited, Middlesex (GB)

( * ) Notice: Subject to any disclaimer, the term of this patent is extended or adjusted under 35 U.S.C. 154(b) by 522 days.

(21) Appl. No.: 11/791,607

(22) PCT Filed: Dec. 12, 2005

(86) PCT No.: PCT/GB2005/004798
§ 371 (c)(1),
(2), (4) Date: Apr. 24, 2008

(87) PCT Pub. No.: WO2006/064212
PCT Pub. Date: Jun. 22, 2006

(65) Prior Publication Data
US 2009/0100912 A1    Apr. 23, 2009

(30) Foreign Application Priority Data
Dec. 15, 2004 (GB) .................................. 0427450.2

(51) Int. Cl.
*G01N 33/00* (2006.01)
(52) U.S. Cl. ..................................................... 73/61.62
(58) Field of Classification Search .................. 73/53.05, 73/61.62, 71.65, 865.6, 866
See application file for complete search history.

(56) References Cited

U.S. PATENT DOCUMENTS

| | | | | |
|---|---|---|---|---|
| 3,684,697 A * | 8/1972 | Gamson | ......................... | 208/131 |
| 4,383,438 A * | 5/1983 | Eaton | ............................ | 73/61.62 |
| 4,624,773 A * | 11/1986 | Hettinger et al. | ......... | 208/120.01 |
| 4,910,999 A | 3/1990 | Eaton | | |
| 5,492,005 A * | 2/1996 | Homan et al. | ............... | 73/61.62 |
| 5,753,802 A * | 5/1998 | Falkler | ......................... | 73/61.62 |
| 5,774,381 A * | 6/1998 | Meier | ............................... | 703/2 |
| 5,959,297 A | 9/1999 | Weinberg et al. | | |
| 6,053,032 A | 4/2000 | Kraus et al. | | |
| 6,062,069 A * | 5/2000 | Panchal et al. | ............... | 73/53.01 |
| 6,978,663 B1 * | 12/2005 | Sinquefield | ................... | 73/61.62 |
| 7,390,664 B2 * | 6/2008 | Fung et al. | ....................... | 436/17 |
| 7,650,782 B2 * | 1/2010 | Taylor et al. | ............... | 73/114.77 |
| 2002/0006667 A1 * | 1/2002 | Chimenti et al. | ............... | 436/60 |
| 2002/0115221 A1 | 8/2002 | LaGraff et al. | | |
| 2003/0172725 A1 * | 9/2003 | Kelemen et al. | ............. | 73/61.63 |
| 2004/0229374 A1 | 11/2004 | Kelemen et al. | | |

FOREIGN PATENT DOCUMENTS

| | | |
|---|---|---|
| EP | 0 608 081 A1 | 7/1994 |
| WO | WO 01/51589 A1 | 7/2001 |
| WO | WO 2004/060551 A1 | 7/2004 |
| WO | WO 2004/061450 A1 | 7/2004 |

* cited by examiner

*Primary Examiner* — John Fitzgerald
(74) *Attorney, Agent, or Firm* — Nixon & Vanderhye

(57) ABSTRACT

The fouling caused by a refinery feedstock on one or more refinery processes, said process comprising: (i) providing a plurality of refinery feedstocks and/or a plurality of fractions of one or more refinery feedstocks, (ii) providing an array comprising a plurality of metal samples representative of metallurgy present in a refinery, (iii) contacting each of the plurality of metal samples with one or more of said (iv) refinery feedstocks or fractions under non-static conditions, and determining the fouling of said refinery feedstock or fraction thereof. Preferably, the metal samples are in the form of a microfabricated array and the testing is carried out in parallel using high throughput experimentation.

14 Claims, No Drawings

PROCESS FOR EVALUATING FOULING CAUSED BY REFINERY FEEDSTOCKS

This application is the U.S. National Phase of International Application PCT/GB2005/004798, filed 12 Dec. 2005, which designated the U.S. PCT/GB2005/004798 claims priority to British Application No. 0427450.2 filed 15 Dec. 2004. The entire content of these applications are incorporated herein by reference.

This invention relates to processes for the evaluation of fouling caused by refinery feedstocks on refinery processes using high throughput experimentation.

Combinatorial or high throughput chemistry has revolutionized the process of drug discovery. See, for example, 29 Acc. Chem. Res. 1-170 (1996); 97 Chem. Rev. 349-509 (1997); S. Borman, Chem. Eng. News 43-62 (Feb. 24, 1997); A. M. Thayer, Chem. Eng. News 57-64 (Feb. 12, 1996); N. Terret, 1 Drug Discovery Today 402 (1996)). Over recent years, a number of high throughput experimentation techniques have been developed to allow significant increases in the ability to synthesize and test catalytic and other materials for useful properties. In general, such techniques have focussed on development of apparatus and methodologies, including the growing use of robots and computers to design experiments and to automate catalyst and materials preparation and testing, to allow rapid and reproducible testing results to be achieved on relatively small scale samples. For example, much effort has gone in to developing preparation and testing apparatus for numerous types of materials and material properties (such as described in U.S. Pat. No. 5,776, 359) and for chemical reactions of interest (such as described in U.S. Pat. No. 5,959,297, U.S. Pat. No. 6,063,633 and U.S. Pat. No. 6,306,658).

In addition, high throughput techniques have been applied to many different analytical techniques, including separation techniques such as chromatography (such as described in U.S. Pat. No. 6,866,786). Also, cost of components has been used as a factor in the design of libraries or arrays (such as described in U.S. Pat. No. 6,421,612). We have now developed high throughput methodologies that can be applied to evaluating the fouling effect of a refinery feedstock on the metallurgy of a refinery process. On a typical refinery, a number of different refinery feedstocks are processed, such as a number of different crude oils. The refinery feedstocks are also usually blends of available feeds, and thus, it is very difficult to predict the effect of the feedstock, such as fouling effects, on the overall refinery process. Typically, a number of assumptions are made on the basis of previous operating experience, but these can usually only provide an approximate prediction.

The present invention provides a method to evaluate the fouling caused by a refinery feedstock in a high throughput manner.

Thus, according to the present invention there is provided a process for evaluating the fouling caused by a refinery feedstock on one or more refinery processes, said process comprising:
(i) providing a plurality of refinery feedstocks and/or a plurality of fractions of one or more refinery feedstocks,
(ii) providing an array comprising a plurality of metal samples representative of metallurgy present in a refinery,
(iii) contacting each of the plurality of metal samples with one or more of said refinery feedstock or fractions under non-static conditions, and
(iv) determining the fouling of said refinery feedstock or fraction thereof.

The present invention provides a process for the evaluation of the effect of a refinery feedstock on fouling in one or more refinery processes that allows the potential process issues of using a refinery feedstock to be evaluated prior to its use, and potentially even before its purchase. The present invention can also aid selection of the most appropriate refinery at which a feedstock should be processed where more than one option is available. Unlike previous methods of testing, the present invention, using high throughput techniques, permits testing to be carried out against a number of different metal samples. Multiple samples of one feedstock may be tested, or a multiplicity of feedstocks and/or fractions, for example all relevant feedstocks and/or fractions, may be tested, against a selected type of metal sample. In effect, an array of feedstocks and/or fractions can be tested against an array of metal samples, to provide a large quantity of data which can be manipulated to provide fouling "maps". The throughput of the overall workflow is important, with the rate of provision of refinery feedstocks and/or fractions in step (a) preferably being at least 50 per week, for example at least 250 per week, especially at least 2000 per week, and the rate of determination of the fouling effect of step (d) preferably being at least 250 per week, for example at least 1250 per week, especially at least 10,000 per week.

The refinery feedstock may be any suitable refinery feedstock, including a crude oil, a synthetic crude, a biocomponent, an intermediate stream, such as a residue, gas oil, vacuum gas oil, naphtha or cracked stock, and blends of one or more of said components, such as a blend of one or more crude oils or a blend of one or more crude oils with one or more synthetic crudes.

In step (ii) of the process of the present invention there is provided a plurality of metal samples representative of metallurgy present in a refinery. Fouling is generally not significantly metal dependent: Therefore, although a wider range of different metal samples may be provided, the plurality of metal samples representative of metallurgy present in a refinery can suitably comprise no or only a few different metallurgies, such as only 1 metal or only 2 to 3 different metallurgies, and the process of the present invention may be (predominantly) used to compare the effects of differences in process conditions during contacting with the refinery feedstock or fraction thereof and/or in the properties of fractions of the refinery feedstock, as described further below.

Typically, the plurality of metal samples will comprise at least 10 metal samples, such as at least 20, for example, at least 50 metal samples. The process of the present invention may be performed using a microfabricated array of metal samples.

The metal samples may be representative of metallurgy present in a particular refinery or of a number of differing metallurgies present in two or more refineries. Metal samples representative of other metallurgies may also be present, but typically the majority of the metals present will be representative of metallurgies already present in one or more refineries.

All or some of the metal samples may have been treated with surface coatings believed to reduce fouling in order that the match of such treatments to the feedstock can be determined. Typical surface coatings include ceramics and certain polymers, such as Teflon.

In step (iii) of the process of the present invention each of the plurality of metal samples is contacted with the refinery feedstock or a fraction thereof.

The plurality of metal samples are preferably each contacted with a refinery feedstock or a fraction thereof in an essentially parallel (rather than a sequential) manner, such that the fouling of each metal sample may be determined in parallel.

The contacting of the refinery feedstock or a fraction thereof with each of a plurality of metal samples may comprise contacting a single stream (being the refinery feedstock or a single fraction thereof) with a plurality of metal samples or may comprise treating a refinery feedstock to produce a plurality of fractions, each of which is contacted with a separate metal sample. Thus, the or each refinery feedstock may be used as is, or may be treated to produce a fraction thereof or a plurality of fractions thereof before contact with the plurality of metal samples.

"Treating" as used herein comprises physical and/or chemical treatment of the refinery feedstock. Physical treatment may comprise division (dividing) of a stream into two or more portions having identical chemical and physical properties to the original stream. For example, the refinery feedstock may be divided to produce a plurality of portions having identical chemical and physical properties to the original refinery feedstock. In the absence of further treatment these portions may be used as fractions. Alternatively, these portions may be further treated to produce fractions. Treatment may also include, for example, blending the refinery feedstock or two or more portions of the refinery feedstock with samples of one or more other refinery feedstocks or distillation or other treatment to give one or more fractions with a narrower boiling range than the original refinery feedstock.

These and other treatments are described further herein.

The refinery feedstock or fraction(s) of the refinery feedstock produced should be representative of the refinery stream that may typically be in contact with the equivalent metallurgy in a refinery process. By "representative of" is meant having at least some similar chemical and/or physical properties as the typical refinery stream to the refinery process. For example, one or more fractions may be produced having boiling point ranges typical for the feedstream to the equivalent process on a refinery.

Chemical and physical properties of the feedstream to a particular refinery process will depend on a particular refinery configuration, but typical properties are described, for example, in Handbook of Petroleum Refining Processes ($2^{nd}$ Edition), edited by Robert A Meyers and published by McGraw-Hill.

For example, in a refinery the metallurgy in the heating section of a crude distillation column typically is exposed to the entire refinery feedstock. Hence, in the present invention, a metal sample may be contacted with the refinery feedstock itself (or a fraction obtained by division thereof) or a fraction obtained by blending of the refinery feedstock with one or more other refinery feedstocks without treatment such as distillation. In contrast, the metallurgy in the pipework and heating before certain process units present in a refinery process after the crude distillation unit is typically only exposed to fractions of said refinery feedstock with limited boiling point ranges, and hence, in the present invention, the refinery feedstock is treated to produce such a representative fraction for contact with an appropriate metal sample. As a further example, in heat exchangers used for crude oil pre-heat prior to distillation, one side of the exchanger is exposed to the crude oil feedstock and the other side to fractions obtained from the distillation, for example, distillate and residue fractions. Hence, in the present invention, the refinery feedstock may be used as is and/or may be treated to produce a representative fraction for contact with an appropriate metal sample(s) for the heat-exchanger.

Fouling in a refinery is particularly an issue with (i) the refinery feedstock itself, i.e. a crude oil, a synthetic crude, a biocomponent or blends thereof, (ii) with the residue fraction obtained from a crude distillation unit (CDU) or blends of such fractions with other residue fractions or with a refinery feedstock, and (iii) with vis-broken fractions (obtained after vis-breaking of the residue fraction). Thus, in the process of the present invention the refinery feedstock or fraction(s) thereof are preferably representative of one of these streams.

Any suitable physical or chemical treatment methods may be used to obtain fractions representative of the typical feedstream for said refinery process in the process of the present invention. For example, treatment in a microdistillation column or microfractionator may be used to obtain fractions with required boiling point ranges. This may be used, for example, to obtain a fraction representative of the residue fraction from a crude distillation unit.

Other physical and chemical treatment techniques may include solvent extraction, membrane treatments, adsorption treatments and suitable chemical reactions. Combinations of techniques may be required, for example, micro-distillation followed by a non-catalytic cracking step may be used to represent crude oil distillation followed by visbreaking, to give a fraction representative of a conventional visbroken fraction.

When the treatment comprises dividing of the refinery feedstock, this may be achieved by any suitable means. For example, dividing may be performed in a batch mode by using one or more automated syringes to provide a plurality of portions. Alternatively, a series of microflow controllers or microvalves may be used in which the flow for each portion is generally continuous, but can be started and stopped, and optionally varied, using the valve or controller. As a further alternative, a plurality of baffles or other flow control means, such as orifices in a plate, where flow cannot be shut-off or varied independently for each portion, but which provide an even flow distribution across a plurality of portions, may be used.

In one embodiment where a fraction with a limited boiling point range (compared to the refinery feedstock) is desired, the refinery feedstock or a portion obtained from the refinery feedstock may be placed on a heating device, and heat applied to increase the sample temperature. The fraction which boils between the desired ranges is collected, for example, by using a suitable valve to collect the fraction of the correct boiling range, which is then cooled to condense said fraction. The heating device may be a heated microoscillator, as described in U.S. Pat. No. 5,661,233.

In another embodiment where a fraction with a limited boiling point range is desired, the refinery feedstock or a portion thereof may be placed in an enclosed channel comprising at least three sections, each section separated by valves or other suitable barriers which liquid samples cannot pass, but gaseous samples can. Thus, a portion may be placed in the first section of a channel and the first section heated to the upper boiling point of the boiling point range desired, for example using a heating laser to give local heating, and the second section may be maintained at ambient temperature (or below), such that all material with a boiling point below the upper boiling point vaporises and passes from the first section into the second section, where it condenses.

The second section is then heated to the lower boiling point of the range desired, for example using a heating laser to give local heating, and the third section is maintained at ambient temperature (or below), wherein all material with a boiling point below the lower boiling point vaporises and passes from the second section into the third section, leaving, in the second section, a fraction with the desired boiling point range.

Alternatively, the second section may maintained at the lower boiling point throughout, such that material with a boiling point above the range desired remains in section 1, material with a boiling point in the range desired is collected in section 2, and material with a boiling point below the range desired is collected in section 3.

A plurality of channels as described in this embodiment, each having the at least three sections may be provided on a spinning disk-type separation device as described in WO 01/87485 or WO 2004/58406, allowing a plurality of fractions to be produced in parallel.

In a further embodiment, further sections comprising one of the plurality of metal samples may also be provided for each channel on a spinning disc, and the contacting of each metal sample with the fraction of a refinery feedstock may also be performed on the spinning disc.

The contacting of each of the plurality of metal samples with the refinery feedstock or a fraction thereof is preferably under conditions representative of those to which the equivalent metallurgy would be exposed in the refinery. Conditions which it is especially preferred are representative include temperatures, flow rates, and turbulence. In one embodiment, these conditions will be equivalent to those in the refinery, such as the same temperature, flow rates and turbulence. In an alternative embodiment, more severe conditions than those to which the equivalent metallurgy would be exposed in the refinery, such as higher temperatures, lower flow rates may be used to enhance fouling rates and enable relative results for different feedstocks to be obtained more rapidly.

The contacting time is another variable and the fouling may be evaluated with time of contacting. The contacting conditions may also be varied with time or, where a plurality of fraction of the refinery feedstock are produced, for contact of another one of the plurality of fractions with another one of the plurality of metal samples such that a range of temperatures and other operating conditions can be evaluated.

Other variables that may be varied, either with time or for contact of another one of the plurality of fractions with another one of the plurality of metal samples include, where appropriate, variation in the boiling point range of the fraction of the refinery feedstock and variation in the blending ratios and compositions obtained by blending the refinery feedstock or a portion thereof with one or more other refinery feedstocks, giving information on the options for mitigating potential problems by process control.

The contacting of each of the plurality of metal samples with the refinery feedstock or fraction thereof is performed under non-static conditions i.e. varying conditions, typically representative of those to which the equivalent metallurgy would be exposed in the refinery. For example, the process may be carried out by continually flowing the refinery feedstock or a fraction thereof over the metal sample, or under sheer (moving, e.g. rotating, the metal sample in the fluid) or turbulence, or under variable temperature or pressure conditions. Thus, conditions which may be varied include temperatures, flow rates, sheer, soak, condensation and/or turbulence. Typically, the results present the fouling rate as a function of flow, shear, temperature, pressure, feedstock and/or fraction.

A range of temperatures and other operating conditions, including variation in the boiling point range of the refinery feedstock fraction where appropriate, can be evaluated, giving information on the options for mitigating potential problems by process control.

Each metal sample may be provided with any desired geometry. The geometry of the sample may change the flow characteristics over the sample, for example the turbulence. For example, a metal film twisted into a spiral may be used to investigate the effects of turbulence on fouling. Various different geometries can be readily provided for samples made using microfabrication techniques.

In step (iv) the fouling of said feedstock on the metals is determined. This may be by any suitable means, such as visual analysis, ellipsometry or surface analysis using a suitable analytical technique, or by measurement of the mass accumulation on the metal samples.

In one preferred embodiment of the present invention, the metal samples are in an initial polished form (e.g. a polished peg) and the or each refinery feedstock or fraction is flowed (as a single stream) over a number of different metals samples which are resistively heated to different temperatures. After flowing the feedstock for a given time the polished surface is investigated by optical means, for example, ellipsometry, or physical means, for example, micro measurement, to determine any deposition of fouling on the surface.

In another preferred embodiment of the present invention, the metal samples are in a form which has a non-negligible resistance, such as wires, thin sheets or meshes. Such samples have the advantage that their resistance, and any changes therein, can be readily measured. Thus, any fouling of the metal samples will be measurable by changes in resistance of the samples. Such samples have a further advantage in that they can be heated and their temperature can be accurately controlled by resistive heating.

In another embodiment the temperature of the feedstock or a fraction thereof before and after contacting with a heated metal sample may be measured to determine the degree of heating of the fluid by the metal sample. As the metal sample becomes fouled the degree of heating will drop. The change in delta temperature with volume of feedstock flowed over the heated metal sample indicates the degree of fouling.

Most preferably, the process of the present invention comprises flowing the refinery feedstock or one or more fractions thereof over a plurality of resistively heated metal wire or mesh samples and measuring the resistance change, or the delta temperature change of the fluid, with time to determine the rate of fouling of said metal samples.

Whatever method of determining the fouling effect of the feedstock and/or fraction is chosen, the determination for each metal sample may be carried out in parallel (i.e. each analysis is carried out simultaneously) or in series, for example using rapid serial analysis.

In a preferred embodiment of the present invention, the asphaltene or wax stability of the refinery feedstock and/or of the one or more fractions thereof may be measured.

The measurement of asphaltene stability for crude oils generally is well-known and is described, for example, in IP 143 (BSI 2000: Part 143) "Determination of asphaltenes (heptane insolubles) in crude petroleum and petroleum products" or ASTM D6560-00 "Standard Test Method for Determination of Asphaltenes (Heptane Insolubles) in Crude Petroleum and Petroleum Products".

A further method for measurement of asphaltene stability (for blends of two or more hydrocarbon liquids) is described in WO 2004/061450.

In the asphaltene stability test according to the present invention, samples of the refinery feedstock or of one or more of the fractions thereof are mixed with solvents (e.g. n-heptane, toluene or mixtures thereof) at different volumes and compositions of solvent and each subjected to vibrational mixing. The asphaltene stability is determined by the onset of flocculation.

Preferably, the solvent addition and vibrational mixing are achieved in an automated manner, for example by means of a robotic workstation. The mixtures may be present in an array of suitable wells, for example, in a micro-titre plate.

The onset of flocculation on addition of the solvents may be determined by any suitable technique, but again this is preferably done in an automated manner, for example using a spectroscopic technique, such as IR, on each mixture and measuring the change in transmission of radiation.

Using the process of the present invention, the potential for fouling problems in various parts of a refinery process from a particular refinery feedstock can be rapidly evaluated. If necessary, mitigation steps, such as by careful process control and/or addition of fouling inhibitors, which can be added specifically as and where needed in the refinery process, can be used. The present invention can be used to test the effectiveness of different chemical treatments, for example different additives or different dosages, to identify optimal treatment for a particular fouling blend. Thus, it is possible to assess the suitability of such fouling inhibitors by addition of such inhibitors to the refinery feedstock or fraction thereof prior to contacting with the metal sample. In such way a number of different potential fouling inhibitors may be assessed against a variety of feedstock blends enabling optimisation of blend and treatment. Further, by providing metal samples coated with particular surface treatments the ability of such treatments to reduce fouling may be determined.

The process of the present invention may also be applied to blends of the feedstock to be evaluated with other feedstocks, and hence used to evaluate the effect of the blended feedstock on the fouling in various parts of a refinery process.

The process of the present invention may be repeated for a number of different potential refinery feedstocks.

The different refinery feedstocks to be evaluated may be separate (independent) feedstocks or may be blends, for example, in different ratios, of two or more other refinery feedstocks.

Alternatively, a number of different potential refinery feedstocks can be evaluated simultaneously, each, or a fraction of each, being fed to a plurality of metal samples representative of metallurgy present in a refinery as described above.

In a preferred embodiment of the present invention, once the determination of the fouling of a refinery feedstock or fraction thereof (on a metal sample) in step (iv) has been performed, suitable refinery process models may be applied to determine the impact of the refinery feedstock. Suitable refinery models are known to the person skilled in the art, and may include, for example, linear programme models for feedstock and product evaluation, process optimisation models, such as for individual process unit optimisation and refinery-wide optimisation, and/or risk-based models, for evaluation of processing impacts of the refinery feedstock.

The process of the present invention will generate a large amount of data on the fouling of refinery feedstocks or fractions thereof. In a further embodiment, this data may be utilised to develop, update, maintain and/or verify process models. For example, a large amount of data may be rapidly produced over a broader parameter set than from pilot plant parameter studies enabling the building of a process model, and further data generated may be utilised to provide continuous update and refinement of the process model (for example, for a wider parameter space).

Modelling or other experimental design-techniques may be used to generate a set of variable process conditions for one or more refinery feedstocks which it is desired to evaluate the fouling for use in the development, updating or verification of one or more process models, and the process of the present invention can be specifically used to evaluate the processes to generate the required data for the process models.

The invention claimed is:

1. A process for evaluating the fouling caused by a refinery feedstock on one or more refinery processes, said process comprising:
   (i) providing a plurality of refinery feedstocks and/or a plurality of fractions of one or more refinery feedstocks,
   (ii) providing an array comprising a plurality of metal samples representative of metallurgy present in a refinery,
   (iii) contacting each of the plurality of metal samples with one or more of said refinery feedstocks or fractions under non-static conditions, wherein each of the refinery feedstocks or fractions is contacted with one of said metal samples in an essentially parallel manner, and
   (iv) determining the fouling caused by said refinery feedstock or fraction thereof, the determination of each metal sample being carried out in parallel.

2. A process as claimed in claim 1 wherein the refinery feedstock to be evaluated is a crude oil, a synthetic crude, a biocomponent, an intermediate stream, or a blend of one or more of said components.

3. A process as claimed in claim 1, wherein the plurality of metal samples comprises at least 20 metal samples.

4. A process as claimed in claim 1, wherein the metal samples are in the form of a microfabricated array.

5. A process as claimed in claim 1, wherein all or some of the metal samples have been treated with surface coatings believed to reduce fouling.

6. A process as claimed in claim 1, wherein each refinery feedstock or fraction thereof is representative of (i) the refinery feedstock itself, (ii) the residue fraction obtained from a crude distillation unit (CDU) or blends of such fractions with other residue fractions or with a refinery feedstock, or (iii) vis-broken fractions.

7. A process as claimed in claim 1, wherein the contacting of each of the plurality of metal samples with the refinery feedstock or a fraction thereof is under temperature, flow rate, and turbulence conditions representative of those to which the equivalent metallurgy would be exposed in the refinery.

8. A process as claimed in claim 1, wherein the fouling is determined by visual analysis, ellipsometry or surface analysis using a suitable analytical technique, or by measurement of the mass accumulation on the metal samples.

9. A process as claimed in claim 1, wherein the temperature of a feedstock or fraction thereof before and after contacting with a heated metal sample is measured to determine the degree of heating of the fluid by the metal sample.

10. A process as claimed in claim 1, wherein the asphaltene or wax stability of a refinery feedstock and/or fraction thereof is measured.

11. A process as claimed in claim 1, wherein the refinery feedstock to be evaluated is treated to produce a fraction thereof or a plurality of fractions thereof and the or each fraction is contacted with the plurality of metal samples.

12. A process as claimed in claim 11, wherein the treatment comprises one or more of division, treatment in a microdistillation column or microfractionator, solvent extraction, membrane treatments, adsorption treatments and suitable chemical reactions.

13. A process as claimed in claim 1, wherein the metal samples are in a form which has a non-negligible resistance, such as wires, thin sheets or meshes.

14. A process as claimed in claim 13 wherein fouling of the metal samples is measured by changes in resistance of the metal samples.

* * * * *